(12) United States Patent
Lam

(10) Patent No.: US 8,506,541 B2
(45) Date of Patent: Aug. 13, 2013

(54) OSTOMY APPLIANCE COMPRISING A WICKING LAYER

(75) Inventor: Peter Kwok Hing Lam, Frederiksberg C (DK)

(73) Assignee: Coloplast A/S, Humlebaek (DK)

( * ) Notice: Subject to any disclaimer, the term of this patent is extended or adjusted under 35 U.S.C. 154(b) by 0 days.

(21) Appl. No.: 13/574,252

(22) PCT Filed: Feb. 1, 2011

(86) PCT No.: PCT/DK2011/050024
§ 371 (c)(1),
(2), (4) Date: Jul. 20, 2012

(87) PCT Pub. No.: WO2011/091801
PCT Pub. Date: Aug. 4, 2011

(65) Prior Publication Data
US 2012/0302981 A1    Nov. 29, 2012

(30) Foreign Application Priority Data
Feb. 1, 2010   (DK) .................................. 2010 70028

(51) Int. Cl.
*A61F 5/44*    (2006.01)
(52) U.S. Cl.
USPC .......................................... 604/338; 604/344
(58) Field of Classification Search
USPC ................................................ 604/344, 338
See application file for complete search history.

(56) References Cited

U.S. PATENT DOCUMENTS

| | | | |
|---|---|---|---|
| 4,865,594 A * | 9/1989 | Thomas | 604/332 |
| 4,973,323 A * | 11/1990 | Kaczmarek et al. | 604/339 |
| 5,203,806 A * | 4/1993 | Broida | 604/338 |
| 5,496,296 A * | 3/1996 | Holmberg | 604/336 |
| 5,545,154 A * | 8/1996 | Oberholtzer | 604/336 |

FOREIGN PATENT DOCUMENTS
WO          9960959          12/1999

* cited by examiner

*Primary Examiner* — Leslie Deak
*Assistant Examiner* — Jordan B Bailey
(74) *Attorney, Agent, or Firm* — Colopast Corp., Coloplast A/S; Nick Baumann

(57) ABSTRACT

An ostomy appliance includes a base plate having an inner radial boundary defining a stoma receiving opening and an outer radial boundary defining an outer edge of the base plate. The base plate has an adhesive layer with a first surface for attaching the base plate to skin surrounding the stoma and a second surface opposite the first surface, and a first liquid impermeable layer having a first surface covering the second surface of the adhesive layer. A second surface opposite of the first liquid impermeable layer is provided with a wicking material abutting the inner radial boundary of the stoma receiving opening. The wicking material extends in a radial direction towards the outer edge of the base plate and away from the stoma receiving opening.

13 Claims, 2 Drawing Sheets

OSTOMY APPLIANCE COMPRISING A WICKING LAYER

FIELD OF THE INVENTION

The present invention relates to an ostomy appliance, and in particular a base plate of an ostomy appliance having a wicking layer for transporting liquid waste from the stoma receiving opening.

BACKGROUND OF THE INVENTION

In connection with surgery for a number of diseases in the gastro-intestinal tract, in many cases, a consequence is that the colon, the ileum or the urethra has been exposed surgically and the patient is left with an abdominal stoma and the effluents or waste products of the body, which are conveyed through these organs, are discharged through the artificial orifice or opening and are collected in a collection bag, which is usually adhered to the skin by means of an adhesive wafer or base plate having an inlet opening for accommodating the stoma.

Throughout the past few decades, a number of different ostomy appliances which have been developed specifically designed to increase the security of a patient in such a way that a leakage of fluidized exudates does not occur between the adhesive wafer or plate and the skin surface. Such a leakage may occur when liquid exudates from the stoma comes in contact with the adhesive surface of the wafer or base plate, where the liquid exudates are often damaging to the adhesive of the base plate.

One method of providing protection for the base plate adhesive is described in WO 03/026541 which discloses a body side member for an ostomy appliance and a corresponding exchangeable sealing disc which covers the surface of the body side member between a coupling means and the stoma and thus protects the surface of the body side member from contact with visceral contents, which in turn protects the adhesive of the body side member.

Another way of providing protection for the base plate is disclosed in WO 99/60959 where an improved ostomy face plate which includes a barrier ring of silicone foam, provided as a seal around the stoma, and a blotter ring disposed between the barrier ring and a barrier seal, where the blotter ring blots up leaking liquid and disperses it around the circumference of the barrier ring, in order to keep liquid from pooling in any portion of the barrier ring. This means that the blotter ring collects and stores liquids which enter the space between the barrier ring and the barrier seal.

SUMMARY OF THE INVENTION

The present invention discloses an ostomy appliance comprising, a base plate having an inner radial boundary defining a stoma receiving opening and an outer radial boundary defining the outer edge of the base plate, where the base plate comprises an adhesive layer having a first surface for adhering the base plate to the skin surrounding the stoma and a second surface opposite the first surface, a first liquid impermeable layer having a first surface covering the second surface of the adhesive layer, and where the second opposite surface of the first liquid impermeable layer is provided with a wicking material abutting the inner radial boundary of the stoma receiving opening and extending in a radial direction towards the outer edge of the base plate and away from the stoma receiving opening.

By providing the base plate with a wicking material, it is possible to protect the adhesive surface of the base plate by absorbing the excess liquid material that gathers around the stoma and by wicking or channelling the material away from the stoma receiving opening, thus reducing the risk of the liquid material eroding or damaging the adhesive surface of the base plate. By reducing the risk of erosion of damage to the adhesive surface of the base plate, the risk of leakage due to failure of the adhesive holding the base plate on the body may be reduced significantly. This is especially advantageous for ostomy appliances that are used for collecting partly or fully liquefied waste from the stoma.

The application of a first liquid impermeable layer between the wicking material and the adhesive layer of the base plate ensures that the liquid material which has been absorbed or wicked into the wicking material is not in direct contact with the adhesive material and will not dilute or seep from the wicking material into the adhesive material in areas where the layer wicking material and the layer of adhesive material are on top of each other.

In one embodiment of the present invention, the first surface of the first liquid impermeable layer may cover the entire second surface of the adhesive layer. This means that the first liquid impermeable layer protects the entire second surface of the adhesive layer from liquid or solid material, such as water or liquid exudates, in such a way that any exudates that may be in the wicking material or that may spill onto the base plate in a direction towards the second surface of the adhesive layer will not erode or damage the adhesive layer. This also means that the wicking material may be positioned anywhere onto the second surface of the liquid impermeable material, without risking that any contents of the wicking material will drip or spread to the adhesive surface.

In one embodiment of the present invention, the first liquid impermeable layer may be a liquid impermeable and gas permeable layer. The skin surrounding a stoma is often very sensitive and vulnerable, as the skin area is covered by an adhesive layer of an ostomy base plate and a combination of the irritation caused by the adhesive, liquid exudates and other irritants linked to the use of an ostomy appliance makes the skin area more vulnerable than other skin areas of the user. As a result thereof, the adhesive layer of an ostomy base plate is often made of a skin friendly hypo-allergenic adhesive made of a material that is adapted to allow the skin to breathe by allowing gasses to permeate through the adhesive layer. This allows vapour to escape from the skin surface and allows oxygen or air to access the skin surface through the adhesive layer. With the provision of having a first liquid impermeable layer that is liquid impermeable and gas permeable, the properties of the skin friendly adhesive may be maintained, even though a liquid impermeable layer is added to the second surface of the adhesive layer. The gas permeable layer allows gaseous material to escape from the adhesive layer via the gas permeable layer and furthermore allows air to permeate into the adhesive layer allowing the skin surface to breathe. In an alternative embodiment, the liquid impermeable layer may be gas and/or vapour impermeable, so that gas or vapour is prevented from penetrating the adhesive layer via the liquid impermeable layer.

In one embodiment of the present invention, the wicking material may cover at least a portion of the area of the base plate extending in a radial direction from the inner radial boundary and to the outer radial boundary of the base plate. This effectively means that if the base plate is circular and the inner radial boundary of the base plate is placed approximately in the centre of the base plate, the radial area of the base plate will surround the inner radial boundary completely, i.e. 360 degrees. The wicking material may be positioned in such a way onto the base plate or the liquid impermeable material that at least a strip of wicking material will extend from the inner radial boundary to the outer radial boundary of the base plate. This means that any liquid material that is absorbed at the inner radial boundary by the wicking material will be wicked, transported, transmitted or channelled in a radial direction towards the outer radial boundary of the base plate, ensuring that the absorbed liquid substance is transported away from the inner radial boundary and/or the stoma and this will reduce the risk of the liquid substance eroding the adhesive layer of the base plate at the inner radial boundary of the base plate. By positioning the wicking material as described above, it is possible to selectively decide in which direction the wicking action is performed and control the transport of the liquids to a predefined position on the base plate or outside the base plate.

The wicking material may be any suitable material for the purpose, which is an absorbent material that is capable of transporting the liquid from one location to another location. The wicking material may of a kind which absorbs and transports the liquid using capillary action, where the structure and the choice of material ensure that the liquid is absorbed into the material. Furthermore, the material may be of a kind where, if the material is fully saturated by liquid and further liquid material is absorbed, the wicking material discharges excess liquid material out of the wicking material or into a deposit area in the base plate or outside the base plate, allowing the wicking material to continue to absorb liquids in situations where there are large amounts of liquid waste from the stoma.

In one embodiment of the present invention, the wicking material may cover the entire surface area of the base plate extending in a radial direction from the inner radial boundary to the outer radial boundary of the base plate. By having the wicking material cover the entire surface area of the base plate, the liquid material may be absorbed by the wicking material in any radial direction away from the inner radial boundary. This ensures that the liquid material may be absorbed by the wicking material irrespective of the physical position of the user, i.e. lying down, standing, sitting, etc., as the wicking material covers the entire radial surface, i.e. 360 degrees, around the inner radial boundary.

In one embodiment of the present invention, the wicking material may be extended from the inner radial boundary of the base plate and may be extruded away from the base plate in a radial and/or axial direction. By extruding the wicking material away from the base plate, it is possible to wick the liquid material out of the base plate and possibly into a deposit area, ensuring that the wicking material which is arranged on the surface area of the base plate is not fully saturated and will continuously be capable of absorbing liquids from around the stoma, at the inner radial boundary of the base plate.

In one embodiment of the present invention, the ostomy appliance may further comprise a collecting bag. The collecting bag is used to collect the waste output from the stoma and ensures that the user may go about his daily routine without risking that the waste from the stoma soils his clothes and ensures the correct disposal of the waste, i.e. the collected waste may be thrown into the toilet or in a waste bin.

In another embodiment of the present invention, the wicking material may be extended from the inner radial boundary of the base plate and is extruded into the collecting bag. By extruding the wicking material into a collecting bag, the collecting bag functions as a deposit for the absorbed liquid material and the wicked liquid may be collected along with the other waste material from the stoma. The wicking material or the wicking structure may be a consecutive piece of wicking material that is lead from the base plate and into the bag.

In order to reduce the risk that the liquid collected into the collecting bag is not wicked from the collecting bag and back into the base plate, i.e. a backflow along the wicking material, an absorbent material, such as a sponge, gel or any suitable absorbent material may be placed inside the bag. This ensures that when the liquid gets into the bag, it is absorbed into the absorbent material of the bag, and the absorbent material confines the liquid inside the material, which means that the liquid material collected inside the bag cannot be wicked back towards the base plate.

In one embodiment of the present invention, the ostomy appliance may be a one piece ostomy appliance. By providing the ostomy appliance as a base plate having a permanently attached bag, it is possible to position the wicking material on the base plate in such a way that any liquid material wicked by the wicking material is directed into the bag, and the bag thus operates as a deposit for the wicked liquid material. Furthermore, the bag may be provided with a channel, in the form of a wicking material, a tubular member or any suitable form to ensure that the liquid waste wicked by the wicking material is directed into a specific area of the bag, such as an absorbent material. Furthermore, this means that when the user has to change his/her ostomy appliance, he/she does not have to worry about where the wicking material will direct the liquid material, as the channels are already provided in the base plate and/or the collecting bag.

In another embodiment of the present invention, the ostomy appliance may be a two piece ostomy appliance. The use of a two piece ostomy appliance is often the preferred solution for a number of users, as such a configuration reduces the need to remove and re-attach the base plate to the skin surface around the stoma. This often reduces the irritation to the skin surface as it allows the user to keep the base plate attached to the skin surface, but allowing the collecting bag to be removed and replaced. The wicking material may be arranged in such a way that the absorbed liquid is transported directly into the collecting bag, by extending a strip of wicking material into the volume of the bag, ensuring that the liquid material is deposited into the bag, or the collecting bag may be provided with a channel or a series of channels that mates with the wicking material of the base plate, ensuring that the absorbed channelled liquid material is directed into the bag.

BRIEF DESCRIPTION OF THE DRAWINGS

The invention will be explained in greater detail below, describing in example and referring to further advantages of the invention with reference to the drawing, in which.

DETAILED DESCRIPTION OF THE DRAWINGS

Figure 1:
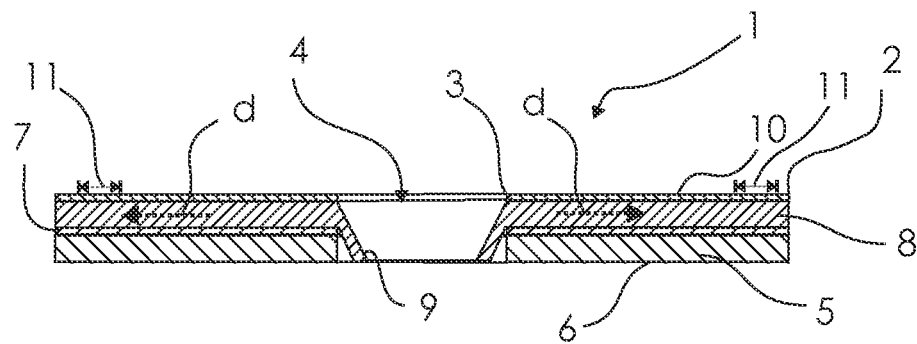
FIG. 1 shows a side sectional view of a base plate according to the present invention.

FIG. 1 shows a side sectional view of a base plate 1 according to the present invention, where the base plate 1 has an outer radial boundary 2 defining the external edge of the base plate 1 and a inner radial boundary 3 defining a stoma receiving opening 4. The base plate 1 is provided with an adhesive layer 5 that ensures that the base plate may be attached to the skin surface of the user, where the skin attaching surface 6 or inner surface of the adhesive layer 5 is attached to the skin surface of the user. A layer 7 of liquid impermeable material is attached to the outer surface of the adhesive layer, where the liquid impermeable layer 7 ensures that liquid cannot come into contact with the outer surface of the adhesive layer 5.

A layer of a wicking material 8 is placed on top of the outer surface of the liquid impermeable layer 7 where the wicking material may be arranged in such a way that a wicking material extension 9 extends into the stoma receiving opening 4 of the base plate 1. In this way any liquid material that exits the stoma but remains inside the stoma receiving opening 4 may be absorbed by the wicking extension 9 and channelled away from the stoma receiving opening and into the wicking material layer 8 of the base plate 1 and towards the outer radial boundary 2 of the base plate. A subsequent layer, backing layer, 10 of liquid impermeable material may be attached to the outer or top surface of the wicking material layer 8, so that the wicking material layer 8 is sandwiched between two layers 7, 10 of liquid impermeable layers, ensuring that any liquids absorbed by the wicking material layer 8 or the wicking extensions 9 is channelled in an outward radial direction (d) away from the stoma receiving opening 4.

The outer surface of the backing layer 10 may be used to connect a collecting bag (not shown) to the base plate 1, either by adhesive coupling, where an adhesive surface on the collecting bag attaches to the outer surface of the backing layer 10, or where the backing layer may be provided with a mechanical coupling positioned on a surface area 11 of the backing layer arranged close to or abutting the outer radial boundary 2, where the mechanical coupling may mate with a corresponding mechanical coupling of a collecting bag.

Figure 2:
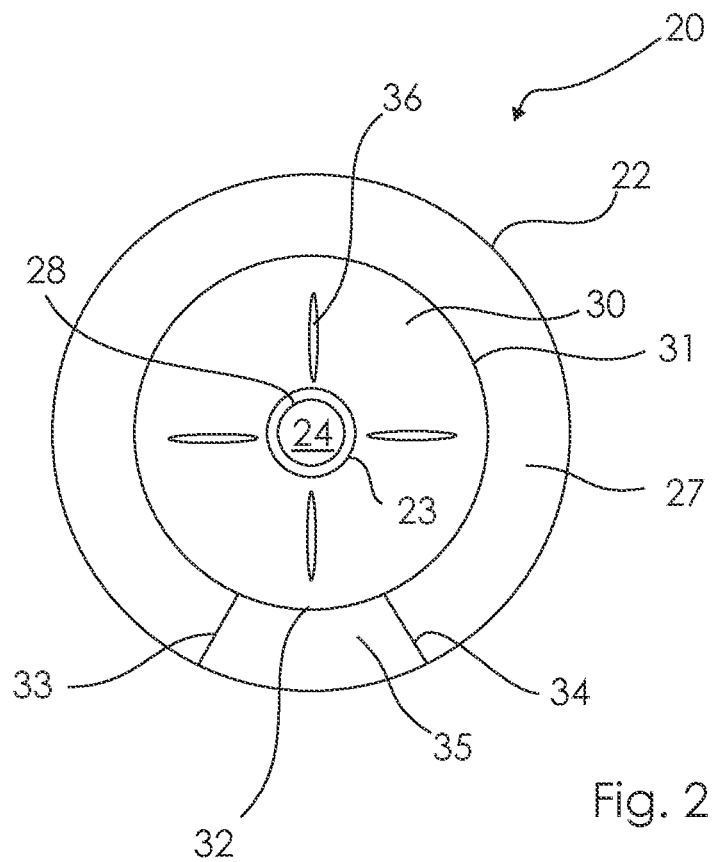
FIG. 2 shows a top view of a base plate according to the present invention.

FIG. 2 shows a top view of a base plate 20 according to the present invention where the base plate has an inner radial boundary 23 defining a stoma receiving opening 24, and a wicking layer 28 that extends into the stoma receiving opening 4. The opposite side (not seen) of the base plate 20 is provided with an adhesive layer having a skin contacting surface, where the top surface of the adhesive layer is provided with a liquid impermeable layer 27 that extends from the inner radial boundary 23 towards the outer radial boundary 22 of the base plate 20.

The wicking layer 28 is arranged on top of the liquid impermeable layer 27, so that any liquid contents inside the wicking layer may be in contact with the liquid impermeable layer 27 and not in contact with the adhesive layer, so that the liquid impermeable layer protects the top surface of the adhesive layer (as seen in FIG. 1). A backing layer 30 is attached to the outer surface of the wicking layer so that the wicking layer is sandwiched between the backing layer 30 and the liquid impermeable layer 27.

In this embodiment, the backing layer 30 is a circular piece of material that is smaller in diameter than the diameter of the liquid impermeable material 27, and the backing layer 30 is welded to the outer surface of the liquid impermeable layer 27, in such a way that the wicking material is enclosed at least in part along its circumference inside the backing layer 30 along a welding seam 31. In one portion along the circular backing layer 30, a gap 32 in the welding seam is provided, arranged in an area between a first 33 and a second 34 outer boundary area defining a discharge channel 35. The wicking material is fixed in place using at least one weld 36 (shown as four welds in this embodiment) where the weld extends from the backing layer 30 through the wicking layer and into the outer surface of the liquid impermeable layer 27.

The configuration of FIG. 2 allows the wicking material 28 to absorb liquid material from the stoma receiving opening 24 and the liquid material is subsequently channelled from the inner radial boundary 23 into the wicking material 28 and may be discharged via the discharge channel out of the base plate.

Figure 3:
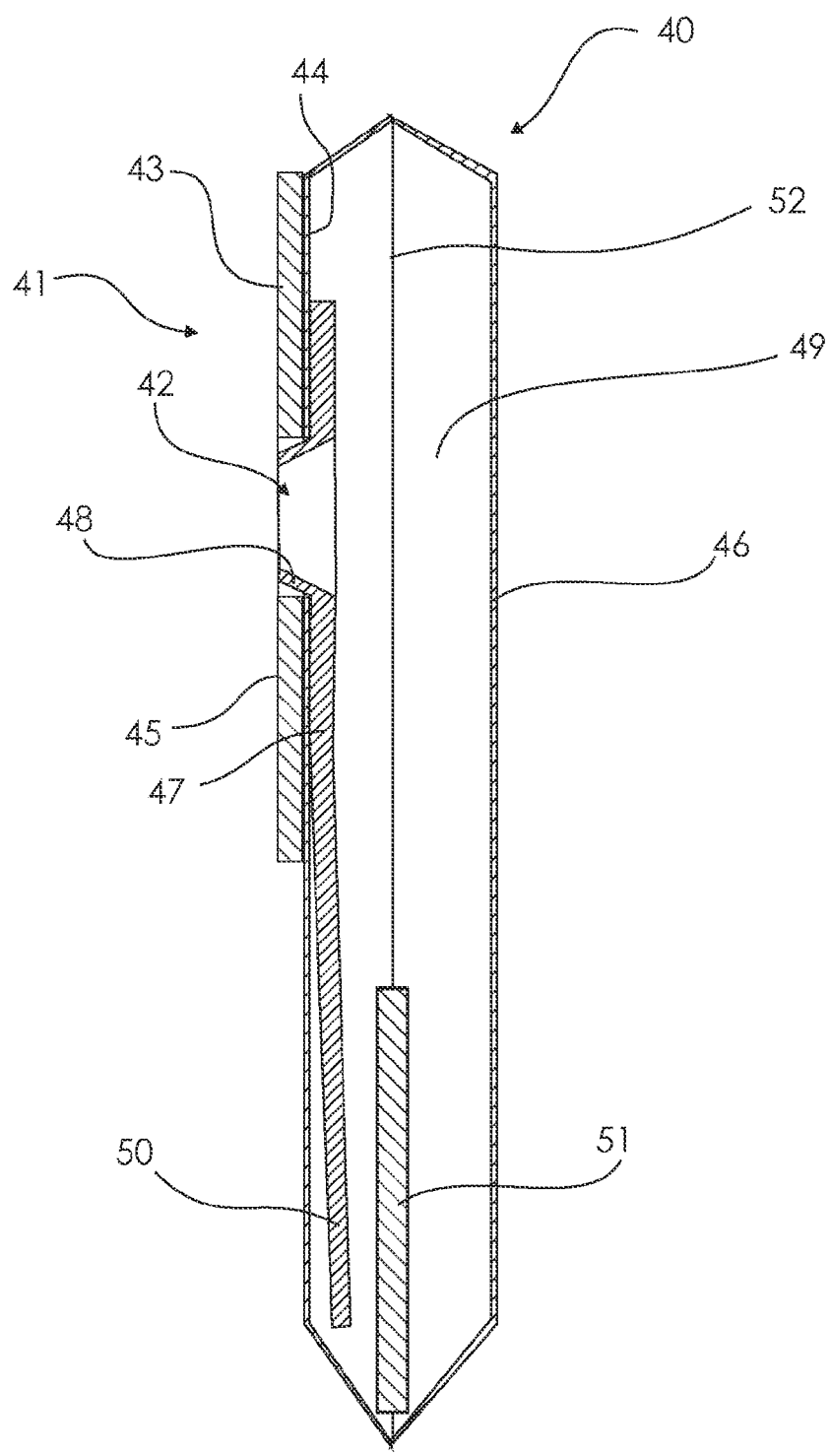
FIG. 3 shows a side sectional view of a one piece ostomy appliance having a base plate and a collecting bag, according to the present invention.

FIG. 3 is a side view of an ostomy appliance 40 according to the present invention, where the ostomy appliance comprises a base plate 41 defining a stoma receiving opening 42 and where the base plate is provided with an adhesive layer 43 having a skin contacting surface 45, and where the base plate is provided with a liquid impermeable layer 44 which may be in the form of the wall of a collecting pouch 46. The ostomy appliance is further provided with a wicking material 47, having an extension 48 that extends into the stoma receiving opening 42 for absorbing liquid material that collects inside the stoma receiving opening.

The wicking material 47 further extends into the inner volume 49 of the collecting bag 46 in the form of a strip 50 of wicking material that extends into the bottom of the inner volume 49 of the collecting bag 46. This ensures that any liquid material absorbed by the wicking material 47 is channelled/transported away from the stoma receiving opening and into the inner volume 49 of the collecting bag 46. In order to ensure that the liquid material cannot flow back from the inner volume 49 of the bag towards the stoma receiving opening, the inner volume of the bag is provided with a portion of an absorbent material 51, which may absorb the liquid material collected in the collecting bag 46. The front and the back wall of the collecting bag 46 are made of traditional collecting bag material and the weld 52 between the front and the back wall may be seen behind the absorbent material 51 in this view.

The invention claimed is:

1. An ostomy appliance comprising:
    a base plate having an inner radial boundary defining a stoma receiving opening and an outer radial boundary defining an outer edge of the base plate, where the base plate comprises
        an adhesive layer having a first surface for adhering the base plate to skin surrounding the stoma and a second surface opposite the first surface,
        a first liquid impermeable layer having a first surface covering the second surface of the adhesive layer,
    and where a second surface opposite of the first liquid impermeable layer is provided with a wicking material abutting the inner radial boundary of the stoma receiving opening and extending in a radial direction towards the outer edge of the base plate and away from the stoma receiving opening.

2. An ostomy appliance according to claim 1, where the first surface of the first liquid impermeable layer covers the entire second surface of the adhesive layer.

3. An ostomy appliance according to claim 1, where the first liquid impermeable layer is a gas permeable layer.

4. An ostomy appliance according to claim 1, wherein the wicking material covers at least a portion of an area of the base plate extending in a radial direction from the inner radial boundary to the outer radial boundary of the base plate.

5. An ostomy appliance according to claim 1, wherein the wicking material covers an entire surface area of the base plate extending in a radial direction from the inner radial boundary to the outer radial boundary of the base plate.

6. An ostomy appliance according to claim 1, wherein the wicking material is extended from the inner radial boundary of the base plate and is extruded away from the base plate in a radial and/or axial direction.

7. An ostomy appliance according to claim 1, further comprising:
 a wicking material extension extending from the wicking material and into the stoma receiving opening of the base plate.

8. An ostomy appliance according to claim 1, further comprising:
 a second liquid impermeable layer attached to an outer surface of the wicking material and arranged so that the wicking material is sandwiched between the first liquid impermeable layer and the second liquid impermeable layer.

9. An ostomy appliance according to claim 7, where the ostomy appliance further comprises a collecting bag.

10. An ostomy appliance according to claim 9, where the wicking material extension extends from the inner radial boundary of the base plate into the collecting bag.

11. An ostomy appliance according to claim 7, where the ostomy appliance is a one piece ostomy appliance.

12. An ostomy appliance according to claim 7, where the ostomy appliance is a two piece ostomy appliance.

13. An ostomy appliance according to claim 9, where the collecting bag comprises an absorbent material arranged in the collecting bag.

\* \* \* \* \*